US008100868B2

(12) United States Patent
Newton et al.

(10) Patent No.: US 8,100,868 B2
(45) Date of Patent: Jan. 24, 2012

(54) ANTI-DRAWBACK MEDICAL VALVE

(75) Inventors: Brian L. Newton, Woonsocket, RI (US); Andrew L. Cote, Sr., Merrimack, NH (US); Charles F. Ganem, Cape Neddick, ME (US); David B. Woyak, Carolina, RI (US); Richard T. Boisjoly, Nashua, NH (US)

(73) Assignee: Nypro Inc., Clinton, MA (US)

( * ) Notice: Subject to any disclaimer, the term of this patent is extended or adjusted under 35 U.S.C. 154(b) by 0 days.

(21) Appl. No.: 12/915,691

(22) Filed: Oct. 29, 2010

(65) Prior Publication Data

US 2011/0046573 A1 Feb. 24, 2011

Related U.S. Application Data

(63) Continuation of application No. 10/895,638, filed on Jul. 21, 2004, now Pat. No. 7,914,502.

(60) Provisional application No. 60/567,639, filed on May 3, 2004, provisional application No. 60/516,126, filed on Oct. 31, 2003, provisional application No. 60/491,486, filed on Jul. 31, 2003.

(51) Int. Cl.
*A61M 5/00* (2006.01)

(52) U.S. Cl. ................ 604/247; 604/246; 604/256

(58) Field of Classification Search .......... 604/246–249, 604/167.01, 167.03, 167.04, 23, 26, 236–238, 604/256, 537; 251/149.1, 149.7
See application file for complete search history.

(56) References Cited

U.S. PATENT DOCUMENTS 5,280,876 A * 1/1994 Atkins ................. 251/149.1
* cited by examiner

*Primary Examiner* — Kevin C Sirmons
*Assistant Examiner* — Laura Schell
(74) *Attorney, Agent, or Firm* — Sunstein Kann Murphy & Timbers LLP

(57) ABSTRACT

A gland member within a medical valve is configured to have a substantially consistent or enlarging internal volume as the valve transitions from a closed mode to an open mode. To that end, the valve has a housing forming an interior containing a flow path, and a stationary post member within the interior. The post member has a lumen that is a part of the flow path. The lumen has an opening to the interior of the housing. The valve further includes a gland member circumscribing the post member to produce a variable volume region formed at least in part between the gland member itself and the post member. In addition, the variable volume region is a part of the flow path, while the gland member occludes the post lumen opening when in the closed mode. The variable volume region has an open volume (i.e., when the valve is in the open mode) that is no less than its closed volume (i.e., when the valve is in the closed mode).

8 Claims, 8 Drawing Sheets

ANTI-DRAWBACK MEDICAL VALVE

PRIORITY

This application is a continuation of U.S. patent application Ser. No. 10/895,638, entitled "Anti-Drawback Medical Valve," filed Jul. 21, 2004, now U.S. Pat. No. 7,914,502, and naming Brian L. Newton, Andrew L. Cote St., Charles F. Ganem, David B. Woyak, and Richard T. Boisjoly as inventors, the disclosure of which is incorporated herein, in its entirety, by reference.

U.S. patent application Ser. No. 10/895,638, in turn, claims priority from from the following provisional United States patent applications, the disclosures of which are incorporated herein, in their entireties, by reference:

Provisional U.S. patent application No. 60/491,486, filed Jul. 31, 2003, entitled, "MEDICAL VALVE WITH STATIONARY POST MEMBER," and naming Andrew L. Cote and Brian L. Newton as inventors, Provisional U.S. patent application No. 60/516,126, filed Oct. 31, 2003, entitled, "ANTI-DRAWBACK MEDICAL VALVE," and naming Andrew L. Cote, Brian L. Newton, and Richard T. Boisjoly as inventors, Provisional U.S. patent application No. 60/567,639, filed May 3, 2004, entitled, "MEDICAL VALVE WITH LOBED GLAND," and naming, Brian L. Newton, Andrew L. Cote and David B. Woyak as inventors.

FIELD OF THE INVENTION

The invention generally relates to medical valves and, more particularly, the invention relates to substantially eliminating fluid drawback in a medical valve.

BACKGROUND OF THE INVENTION

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

To those ends, as a preliminary step, medical personnel insert a syringe into a medical valve that is appropriately secured to a patient. For example, the valve may be coupled to a catheter having an opposite end secured within the patient's vain. Once inserted, fluid may be freely injected into or withdrawn from the patient. Problems arise, however, when the syringe is withdrawn from the valve. Specifically, a back pressure (i.e., a proximally directed pressure) produced by the withdrawing syringe undesirably can cause blood to be drawn proximally into the valve (e.g., via an attached catheter). In addition to coagulating and impeding the mechanical operation of the valve, blood in the valve (or in the catheter) also compromises its sterility.

SUMMARY OF THE INVENTION

In accordance with one aspect of the invention, a gland member within a medical valve is configured to have a substantially consistent or enlarging internal volume as the valve transitions from a closed mode to an open mode. To that end, the valve has a housing forming an interior containing a flow path, and a stationary post member within the interior. The post member has a lumen that is a part of the flow path. The lumen has an opening to the interior of the housing. The valve further includes a gland member circumscribing the post member to produce a variable volume region formed at least in part between the gland member itself and the post member. In addition, the variable volume region is a part of the flow path, while the gland member occludes the post lumen opening when in the closed mode. The variable volume region has an open volume (i.e., when the valve is in the open mode) that is no less than its closed volume (i.e., when the valve is in the closed mode).

In some embodiments, the variable volume region is closed when in the closed mode. Moreover, the gland member may move radially outwardly as the valve transitions from the closed mode toward the open mode. In such case, the radial outward motion may substantially unocclude the opening to the post member lumen.

To provide an anti-drawback effect, the open volume may be greater than or substantially equal to the closed volume. In some embodiments, the gland member has a proximal end that is substantially flush with or extends proximally of a proximal port of the housing. To provide a second reusable seal, the proximal end of the gland may have a slit.

The gland member also may have a sealing ridge that occludes the post lumen opening when in the closed mode. Moreover, the gland member may include a main wall section and a lobed portion. The main wall thickness is greater than the lobe portion wall thickness. In fact, the lobed portion may extend radially outwardly from the main wall section. The lobed portion may move radially outwardly as the valve moves toward the open mode.

In various embodiments, when in the closed mode, the variable volume region is bounded by the post member and the gland member only. To provide an anti-drawback effect, the flow path illustratively has a total volume that varies as the variable volume region varies. For example, the flow path total volume may increase as the volume of the variable volume region increases.

In accordance with another aspect of the invention, a medical valve has a housing forming an interior, and a stationary post member within the interior. The post has a lumen for channeling fluid through the interior. The valve also has a gland member within the interior of the housing. The gland member forms a variable volume region that also is bounded by the post member. The gland member occludes the lumen when in the closed mode. The variable volume region has a closed volume when in the closed mode and an open volume when in the open mode. The open volume is no less than the closed volume.

In accordance with another aspect of the invention, a medical valve has a housing forming both an interior and a distal port. The valve also has a gland member within the interior of the housing. The gland member has a main portion and a protruding portion that together form a variable volume region. The protruding portion protrudes radially outwardly relative to the main portion. Moreover, the protruding portion is defined by a protruding wall, while the main portion is defined by a main wall portion. The protruding wall has a thickness that is less than the thickness of the main wall. In a manner similar to other aspects, the variable volume region has a closed volume when in the closed mode and an open volume when in the open mode. The open volume is no less than the closed volume to substantially prevent net fluid drawback into the interior through the distal port. In other words, during a substantially complete stroke of the valve from the open mode to the closed mode, the total amount of drawn back fluid remaining in the valve should be no greater than about zero microliters.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

In illustrative embodiments of the invention, a medical valve is configured to substantially eliminate fluid drawback when a nozzle or syringe is withdrawn from it. Specifically, in one such embodiment, the medical valve produces neither a net negative nor a net positive pressure when a nozzle or syringe is withdrawn. Consequently, after the nozzle is withdrawn, the net fluid expelled from or drawn into the valve is substantially equal to zero.

To these ends, illustrative embodiments of the medical valve have a fluid path with a volume that is substantially the same when it is in either an open mode (i.e., permitting fluid flow, also referred to as "open position") or a closed mode (i.e., preventing fluid flow, also referred to as "closed position"). More specifically, a portion of the fluid path is formed from a resilient member disposed over a stationary member. When transitioning from the closed mode toward the open mode, the resilient member both expands radially and compresses longitudinally. This expansion and contraction is sized and configured to ensure that the overall volume within the fluid path remains substantially constant as the valve transitions from the closed mode to the open mode. In a similar manner, when retracting back to the closed mode, the resilient member operates in an opposite manner, thus further maintaining the fluid path volume. Details of this and related embodiments are discussed below.

In other embodiments, the valve produces a positive, distally directed pressure (i.e., toward its outlet) when a nozzle or syringe is withdrawn. Such pressure should prevent fluid from being drawn into the valve at such time. To these ends, the expandable member is sized and configured to expand the fluid path volume as the valve transitions toward the open mode, and reduce the fluid path volume as the valve transitions toward the closed mode. Details of this and related embodiments also are discussed below.

Figure 1:
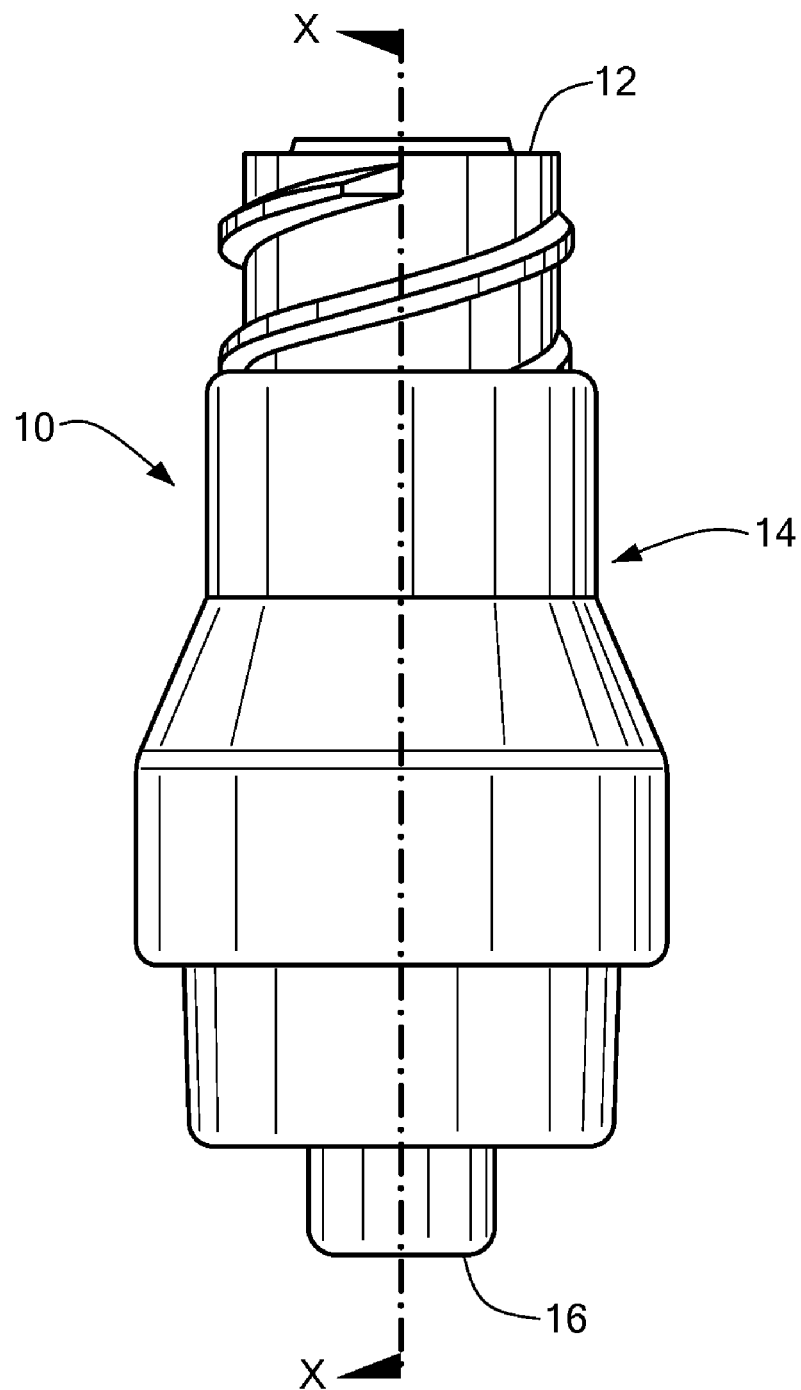
FIG. 1 schematically shows a medical valve that may be configured in accordance with various embodiments of the invention.

FIG. 1 schematically shows a medical valve 10 that is configured to reduce fluid drawback (a/k/a "back-flow" and "reflux") when a syringe or other type of nozzle is withdrawn from it. The valve 10 includes a proximal port 12 for receiving the nozzle, a valve body 14 having an internal valve mechanism (shown in FIGS. 2-5) that controls fluid flow through the valve 10, and a distal port 16 for directing fluid between the valve 10 and a patient. The distal port 16 of the valve 10 may be at its location shown in FIG. 1, at a location that is orthogonal to the longitudinal dimension of the valve 10, or at some other location. The fluid preferably is in liquid form, such as liquid medication. Although much of the discussion herein refers to the proximal port 12 as a fluid inlet, and the distal port 16 as a fluid outlet (also referred to herein as "outlet 16"), the proximal and distal ports 12 and 16 also may be respectively utilized as outlet and inlet ports.

The valve 10 illustratively is a swabbable, luer activated valve. The top surface of the valve mechanism thus should be substantially flush with, or extend slightly outwardly from, the proximal port 12. As known by those in the art, this arrangement permits the top surface of the valve mechanism to be easily cleaned with a swab or other cleaning apparatus. In other embodiments, however, the valve 10 is not a swab valve.

FIGS. 2-5 show four different embodiments of the valve 10 shown in FIG. 1. Identical reference numbers are used, however, across all figures. For example, although they are different embodiments, each embodiment of the valve is identified in the drawings and description that follows by reference number "10." As a second example, each embodiment has a gland, which is identified in all the relevant figures by reference number "28." Their identical reference numbering, however, should not be interpreted to imply that they are identical in structure and function. As noted below, each valve and gland (among other elements) may operate differently to some extent. Other elements, however, may operate identically.

Figure 2:
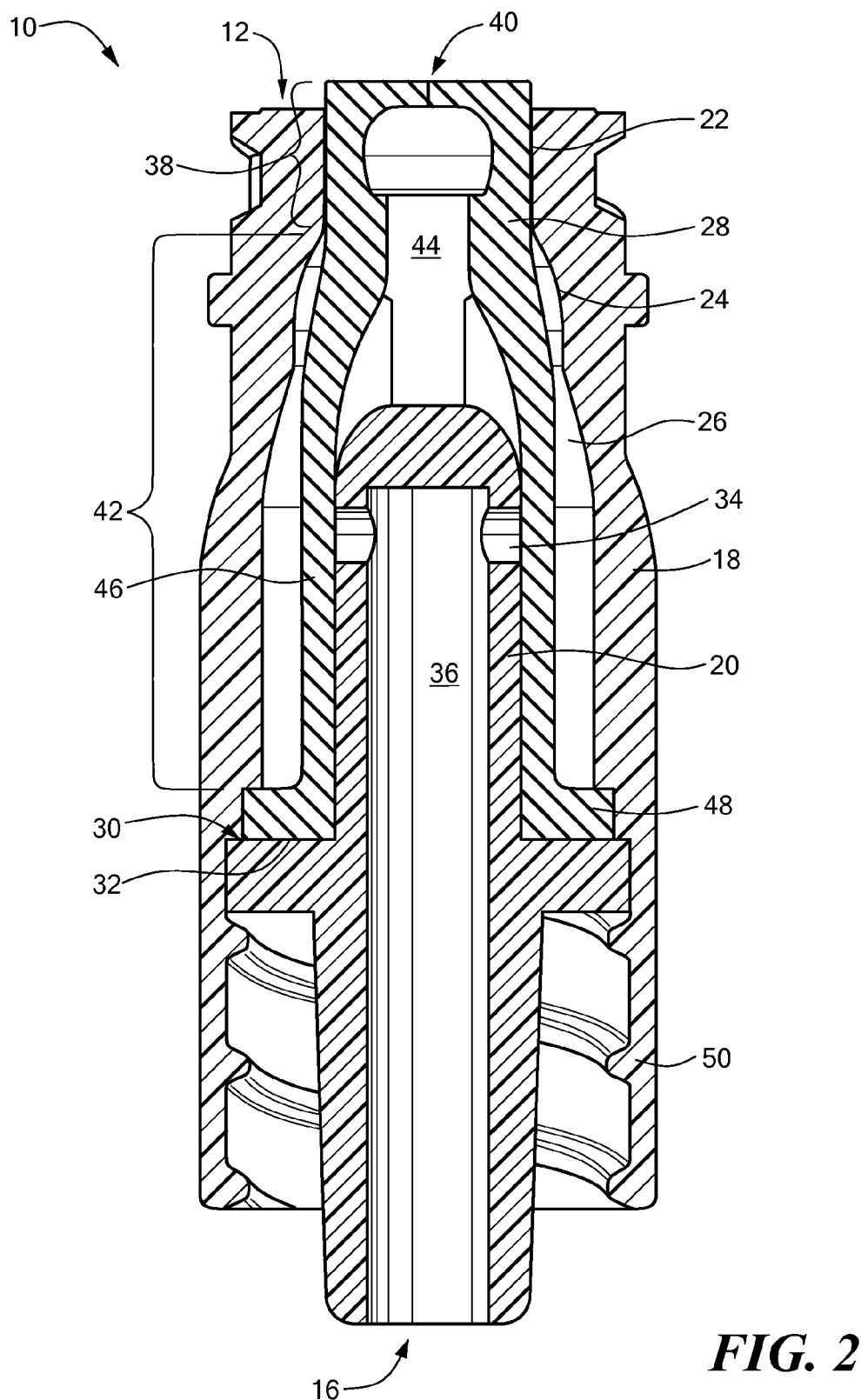
FIG. 2 schematically shows a cross-sectional view of the medical valve of FIG. 1 along line X-X in accordance with a first embodiment of the invention.

FIG. 2 schematically shows a cross-sectional view of one embodiment of the medical valve 10 (along line X-X of FIG. 1) in a closed position. More particularly, the arrangement in FIG. 1 permits the valve 10 to substantially eliminate fluid drawback when a syringe or other type of nozzle is withdrawn from it. As noted above, this reduction can result in either a positive pressure (or displacement) at the distal port 16, or a zero net pressure at the distal port 16.

Among other things, the valve 10 includes a unitary housing 18 that is coupled with a hollow post member 20 terminating at a convex proximal portion. The interior of the housing is contoured to provide the anti-drawback effect with different types of nozzles. Specifically, the interior is contoured to have a tapering proximal region 22 to accept a nozzle, and a longitudinally adjacent, distally diverging region 24. The proximal region 22 illustratively is contoured to accept various types of nozzles, such as those complying with ISO/ANSI standards (e.g., lures complying with ISO/ANSI standards). In addition to the proximal and diverging regions 22 and 24, the interior also has a central region 26 having a significantly larger inner dimension than that of the diverging region 24.

The valve interior contains a resilient, compressible and stretchable member (hereinafter "gland 28") that, in conjunction with the post member 20, controls fluid flow through the valve 10. In illustrative embodiments, the gland 28 is secured within the valve 10 between an interior ledge 30 of the housing 18 and a radial surface 32 of the post member 20. Details of the interaction of the post member 20 and the gland 28 are discussed below.

In the embodiment shown in FIG. 2, the post member 20 has a closed proximal end and a transverse channel 34 (near the proximal end of the post member 20) that leads to an internal post member flow channel 36 (a lumen through the post member). The post member flow channel 36 terminates at the distal port 16. Accordingly, when open, fluid can flow into the post member 20 via the transverse channel 34, through the post member flow channel 36, and out the distal port 16. In alternative embodiments, rather than use a transverse channel 34, fluid can access the post member flow channel 36 via an opening (not shown) in the proximal end of the post member 20. Such alternative embodiment, however, may have a single seal only (see discussion below), or be configured to further seal the noted opening.

The gland 28 is the only movable part within the interior of the valve 10. To that end, the gland 28 has a swabbable seal section 38 having a normally closed slit 40 therethrough, and a tubular section 42 extending from the seal section 38 to its base. When closed, the volume formed by the gland 28 and the post member 20 is considered to be a closed volume. As noted below, this volume is no longer considered to be closed after the gland 28 is urged distally a sufficient amount so that the slit 40 opens or the transverse channel 34 is not occluded. This volume is referred to herein as the "variable volume region." It is anticipated, however, that principles of various embodiments can be applied to other types of variable volume regions, such as those formed by other or additional components. Accordingly, discussion of the noted variable volume region is exemplary and not intended to limit all embodiments of the invention.

The tubular section 42 has two sub-sections; namely, 1) a normally hollow proximal tube section 44 that, when in the closed mode, is proximal of the post member 20, and 2) a distal tube section 46 normally substantially circumscribing and flush against the post member 20. Due to a radially compressive force against the post member 20 (e.g., an interference fit), the distal tube section 46 normally occludes the transverse channel 34, consequently acting as a second seal when in the closed mode. In addition to the seal and tubular sections 38 and 42, the gland 28 also has an attachment section 48 secured between the post member 20 and housing 18 (as noted above).

When closed, which is its normal state, the valve 10 uses its two redundant seals to prevent fluid communication between the proximal and distal ports 12 and 16. Specifically, the gland 28 prevents fluid flow through the transverse channel 34, while the slit 40 prevents fluid flow through the seal section 38. In some embodiments, the gland/transverse channel seal can withstand higher backpressures than those that the slit 40 can withstand.

Insertion of a nozzle against the surface surrounding the slit 40 at the proximal end of the gland 28 opens the valve 10. Specifically, insertion of the nozzle causes the seal and tubular sections 38 and 42 of the gland 28 to both compress and move distally. Consequently, the slit 40 opens and the seal section 38 both axially compresses and radially expands. In a similar manner, the tubular section 42 both axially compresses and radially expands into/within the central region 26 of the valve interior. At some point in the transition from the closed mode to the open mode, the tubular section 42 no longer contacts (i.e., no longer occludes) the transverse channel 34, consequently fully opening the valve 10. Those in the art can configure the radially inward pressure of the gland 28 (at the transverse channel 34) so that the valve 10 opens after the nozzle has been inserted a pre-specified amount.

When open, the variable volume region is considered to have an "open volume," which is based upon noted axial compression and radial expansion. In a corresponding manner, when closed, the variable volume region is considered to have a "closed volume." In illustrative embodiments, the materials and dimensions of the gland 28 are selected to ensure that 1) both the open and closed volumes are substantially equal, or 2) the open volume is greater than the closed volume.

Because, in this embodiment, other regions of the fluid path are substantially constant, the total volume for containing fluid within the fluid path of the valve 10 changes in a manner that corresponds to the variable volume region. Accordingly, if volume of the variable volume region increases, the overall volume of the fluid path increases. In a similar manner, if the volume of the variable volume region decreases, the overall volume of the fluid path decreases.

When the open and closed volumes are substantially equal, there should be no appreciable net positive or negative pressure at the distal port 16 during the stroke of the nozzle as it is withdrawn (i.e., the "withdrawal stroke"). In particular, it is anticipated that during the withdrawal stroke, the variable volume region may not maintain an exactly constant volume—it may fluctuate. In such case, at certain points during the withdrawal stroke, the distal port 16 may draw in small amounts of fluid. At other points during the withdrawal stroke, however, the distal port 16 may expel small amounts of fluid. In either case, there may be some negligible reflux and positive expulsion of fluid from the distal port 16. Various embodiments with substantially equal open and closed volumes, however, ensure that the net fluid in or out of the distal port 16 (i.e., the net amount of fluid during the entire withdrawal stroke) is no greater than a negligible amount. In some embodiments, the valve 10 can be configured to ensure that the volumes remain substantially constant at least after the transverse channel 34 is opened.

Conversely, when the open volume is greater than the closed volume, a positive pressure develops at the distal port 16 when the nozzle is withdrawn. Accordingly, in that case, an appreciable amount of fluid within the valve 10 is expelled from the distal port 16. Expelling the fluid should prevent fluid from being drawn into the valve 10 at that time.

The valve 10 may be manufactured in accordance with conventional processes. For example, the housing 18 and post member 20 may be produced from a rigid plastic, while the gland 28 may be formed from a medical grade elastomeric material, such as silicone or rubber. Other materials having similar properties may be used, however, as long as they can perform the functions discussed herein.

During assembly, the gland 28 first may be inserted into the housing 18, and the post member 20 then may be secured to the housing 18. Other assembly methods, however, first may couple the gland 28 and post member 20 as a single (uncoupled) assembly. The assembly then may be inserted into the distal end of the housing 18. Of course, other methods of assembling the valve 10 may be used. Accordingly, discussion of specific methods are exemplary and not intended to limit the scope of various embodiments of the invention. In either case, the housing 18 and post member 20 may be secured together by conventional means, such as by a snap-fit connection. Alternatively, the housing and post member 20 may be secured together by ultrasonic welding.

Figure 3:
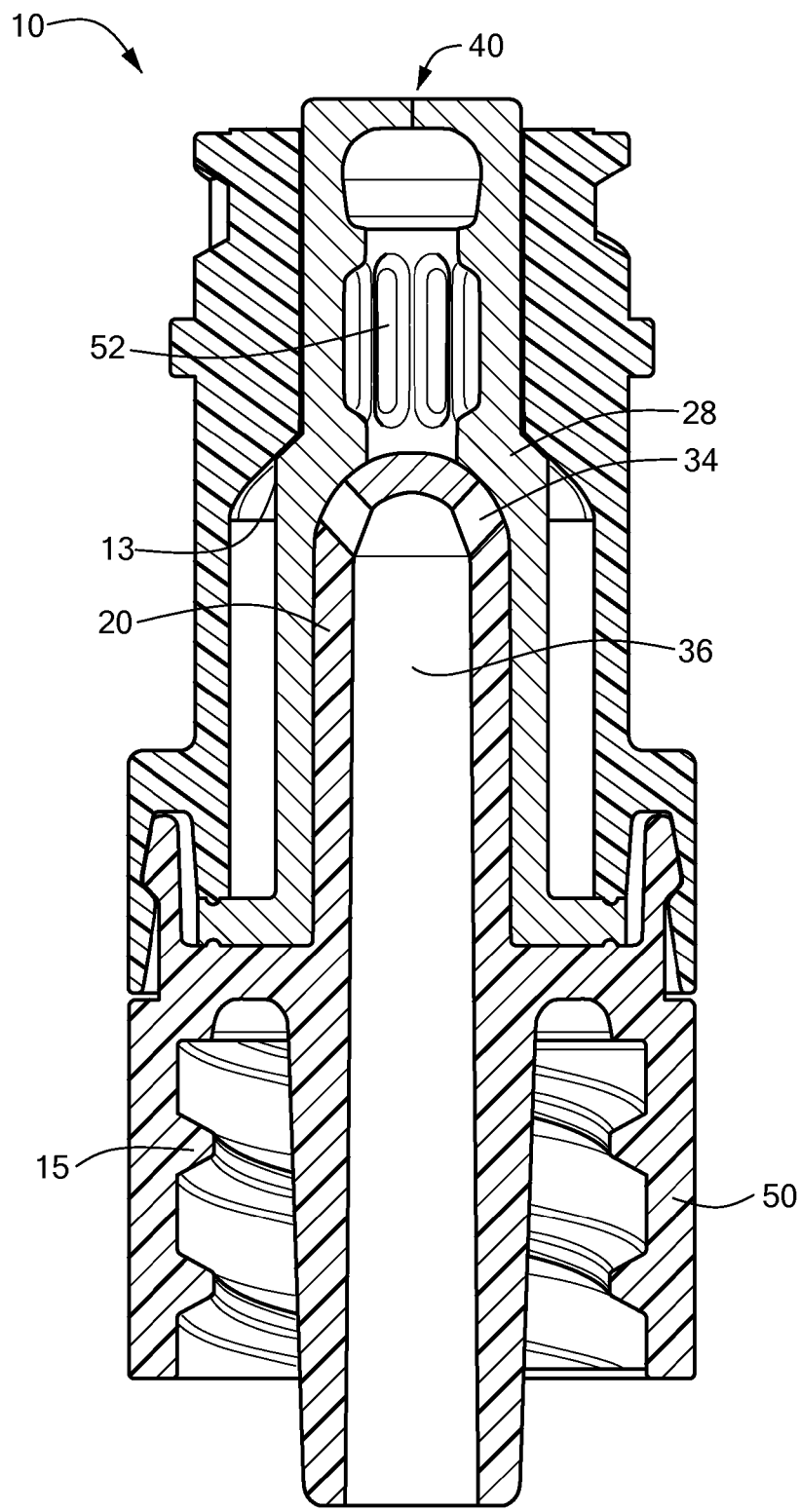
FIG. 3 schematically shows a cross-sectional view of the medical valve of FIG. 1 along line X-X in accordance with a second embodiment of the invention.

FIG. 3 schematically shows a cross-sectional view of a second embodiment of the medical valve 10 shown in FIG. 1. The housing 18 includes a proximal housing portion 13 that couples with a distal housing portion 15. Among other things, the distal housing portion 15 includes a threaded skirt 40, a post member 20, and a mechanism to couple with the proximal housing portion 13. In the embodiment shown in FIG. 3, a snap fit mechanism is used. As noted above, however, other conventional coupling methods may be used.

The gland 28 in the embodiment shown in FIG. 3 also has a plurality of thinned sections 52 within a gland portion that fits over the post member 20. The thinned sections 52 facilitate gland stretching over the post member 20 while maintaining a sufficient column strength to force the gland 28 distally.

Figure 4:
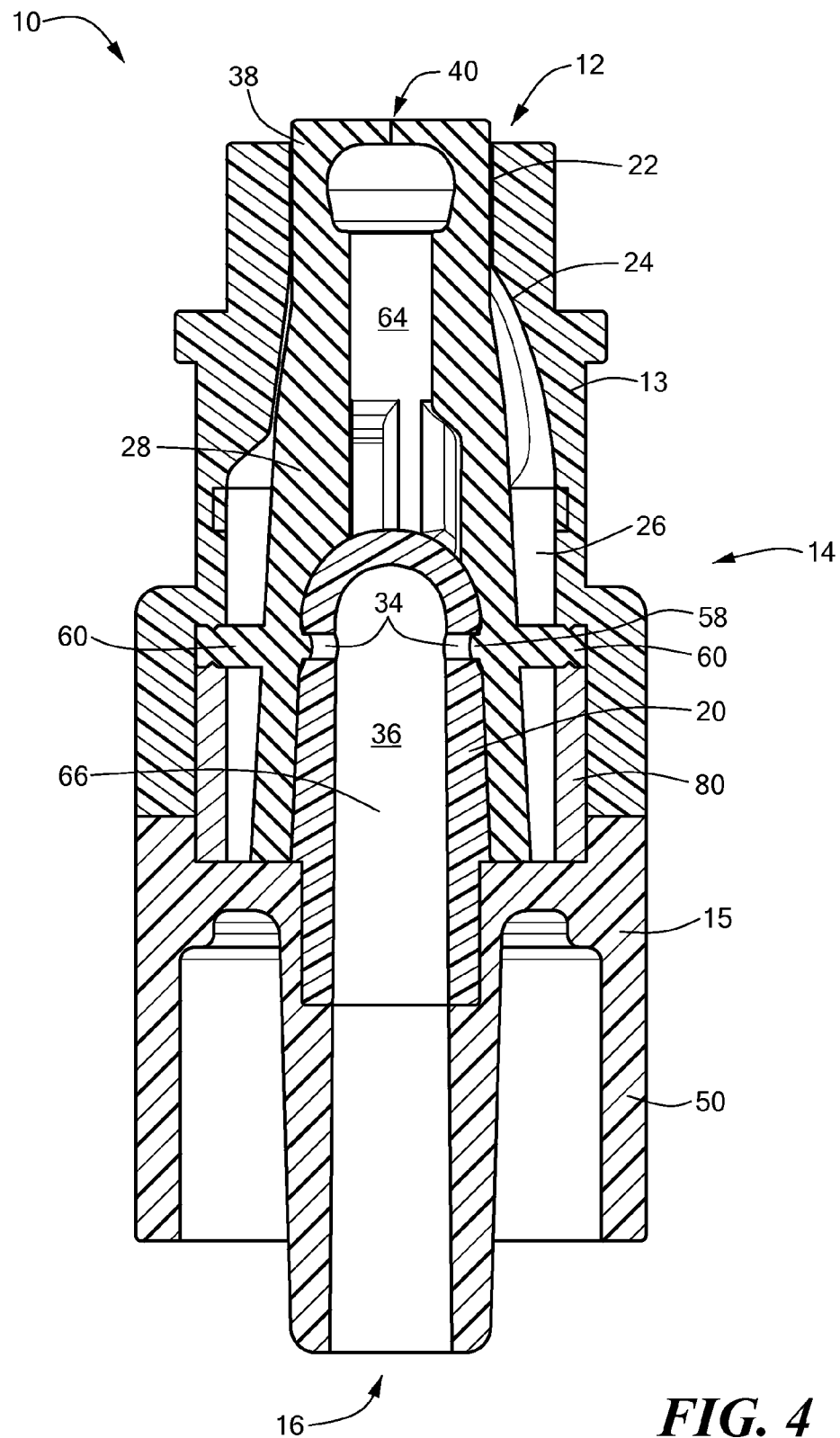
FIG. 4 schematically shows a cross-sectional view of the medical valve of FIG. 1 along line X-X in accordance with a third embodiment of the invention.

FIG. 4 schematically shows a cross-sectional view of a third embodiment of the medical valve 10 shown in FIG. 1 along line X-X. This embodiment of the valve 10 illustratively is produced from three components; namely, a proximal housing portion 13 having the inlet 12, a distal housing portion 15 having the outlet 16, and a gland 28. The two housing portions 18 and 20, which are formed from a hard plastic material, are snap-fit or welded together to form the valve body/housing 14.

In a manner similar to other embodiments, the housing portions 18 and 20 form a specially shaped interior. Specifically, the interior has a tapering proximal region 22 to accept a nozzle, a longitudinally adjacent, distally diverging region 24, and a larger central region 26. These regions illustratively are similar to those corresponding regions discussed above with reference to FIG. 2.

The distal housing portion 15 also has a stationary, hollow post member 20 that terminates at a convex proximal portion. A hoop groove (hereinafter "groove 54") having two through-holes illustratively is circumferentially formed around the outer surface of the post member 20. The through holes effectively form the transverse channel 34 and thus, also are identified by reference number 34. The two through-holes 34 form ports to a flow channel 36 extending through the post member 20.

In accordance with illustrative embodiments of the invention, the valve 10 also has a resilient, compressible, and stretchable gland 28 positioned about the post member 20 and secured between the proximal housing portion 13 and distal housing portion 15. More specifically, the gland 28 illustratively is positioned over the post member 20 to normally occlude fluid flow through the valve 10 when in the closed mode. To that end, the gland 28 has a sealing ridge 58 extending radially inwardly from its interior wall. To ensure a close fit with the post member 20, the sealing ridge 58 normally is in registry with the groove 54 when in the closed mode. Accordingly, the groove 54 and sealing ridge 58 are formed to be complimentarily shaped to close the two through-holes 34 when mated.

To ensure a secure fit between the sealing ridge 58 and groove 54, the gland 28 is secured within the housing interior in a manner that normally applies a radially inward pre-load force. To that end, the sealing ridge 58 is a part of a sealing ring 60 that normally is compressibly secured between the proximal and distal housing portions 13 and 15. Moreover, the sealing ring 60 normally is under a radially compressive force that ensures a secure fit within the groove 54, thus occluding fluid flow through the two through-holes 34. The amount of radial force can be selected during design to ensure that this portion of the valve 10 effectively forms a high pressure seal that can withstand relatively large back pressures (e.g., those higher pressures that may occur during anticipated use, such as pressures up to or greater than about 60 p.s.i.). Other embodiments, however, eliminate the pre-load.

In illustrative embodiments, the gland 28 also has a seal section 38 that normally is flush with, or extends slightly above, the inlet 12 of the valve 10. Accordingly, in a manner similar to other embodiments, the valve 10 is considered to be a "swabbable" luer activated valve. The seal section 38 is configured to act as a low pressure seal. More specifically, the seal section 38 has a normally closed slit 40. When inserted into the inlet 12, a nozzle or syringe deforms the seal section 38, consequently opening the low pressure seal.

In various embodiments discussed herein, the slit 40 is normally closed when the gland 28 is not mounted within the housing 14. No radial force thus is required (by the housing 14) to close the slit 40. In fact, in some embodiments, the outer dimension of the seal section 38 is smaller than the inner dimension of the inlet 12. In alternative embodiments, however, the inner dimension of the inlet 12 is smaller than the outer dimension of the seal section 38 of the gland 28. Consequently, in such embodiments, the housing 14 squeezes the seal section 38, thereby forcing the slit 40 closed. Those skilled in the art may shape the inlet 12 to ensure closure of the slit 40 when the valve 10 is in the closed mode.

As noted above, it is anticipated that the high pressure seal can withstand relatively high pressures. Accordingly, due to the performance of the high pressure seal, it is not necessary for the low pressure seal (i.e., the slit 40 through the seal section 38) to resist large back pressures. In some embodiments, however, the low pressure seal also may be formed to resist relatively high back pressures.

In addition to the seal section 38 and sealing ring 60, the gland 28 also has a main section 62 extending distally from the somewhat loosely defined distal end of the seal section 38 to a proximally facing interior surface of the housing 14. In fact, the sealing ring 60 extends radially outwardly from the main section 62 of the gland 28. The valve 10 thus has a fluid path with two portions; namely, a dynamic portion 64 primarily formed by the gland 28 (i.e., the variable volume region), and a static portion 66 partially formed by the post member 20. More specifically, the dynamic portion 64 generally includes the region formed between the gland 28 and the post member 20. This portion 50 thus extends from the slit 40, through the gland main section 62 to the two through-holes 34 in the post member 20, and to the base of the housing interior. The static portion 66 extends from the interior of the post member 20 to the outlet 16. In other words, the lumen through the post member 20 forms the static portion 66.

In a manner similar to other embodiments discussed above, the main section 62 of the gland 28 is both longitudinally compressible and radially expandable to vary the volume of the dynamic portion 64 of the fluid path. In particular, when a nozzle (e.g., a luer) is inserted into the inlet 12, the seal section 38 of the gland 28 collapses to deform the slit 40 (as noted above). At the same time, however, the main section 62 of the gland 28 should both longitudinally compress and radially expand. When a sufficient amount of radial force is applied to the gland main section 62, the sealing ridge 58 moves radially outwardly from its registration contact with the groove 54. In other words, when the radial force at the sealing ring 60 is equal to or slightly greater than the pre-loaded, radially inward compressive force applied by the sealing ring 60, the sealing ridge 58 moves radially outwardly from occluding contact with the through-holes 34. Consequently, the two through-holes 34 open, thus permitting fluid flow through the valve 10.

As noted above, in some embodiments, the compressive and expansive operation of the gland 28 (in response to an inserted nozzle) causes the shape of the dynamic portion 64 of the flow path to change. Although its shape changes, neutral embodiments are configured to ensure that the net volume of the dynamic portion 64 remains substantially constant as the valve 10 transitions between open and closed modes. To that end, the amount of clearance between the interior wall of the proximal housing portion 13 is selected as a function of the anticipated compressive properties of the gland 28. As a result, the outlet 16 should not develop a non-negligible positive or negative pressure and thus, eliminate non-negligible fluid drawback.

In alternative embodiments, although the interior volume of the dynamic portion 64 of the fluid path is substantially the same at both the open and closed positions, it may fluctuate as the valve 10 transitions between such positions. In yet other embodiments, the interior volume is greater when the valve 10 is in the open position than when it is in the closed position. In such case, the valve 10 produces a distally directed positive pressure through the outlet 16 when closing. Accordingly, in such embodiment, fluid is forced out through the outlet 16 as the valve 10 moves toward the closed position.

In some embodiments, the interior volume of the gland 28 depends upon the depth of penetration of the nozzle. Specifically, the internal volume may remain substantially constant to a specified depth within the valve 10. Further distally directed insertion, however, may cause the internal gland volume to increase. In yet other embodiments, depending upon the longitudinal depth of the nozzle, the interior volume of the valve 10 may have both specified amounts of fluid drawback and distally directed fluid pressure at different times during its travel between open and closed positions. Stops (not shown) may be inserted in the interior of the housing 14 to limit the insertion depth of a nozzle.

The gland 28 should operate as intended by properly selecting the various gland and housing design parameters. For example, among other things, the gland durometer and flexibility (modulus) are selected to coordinate with the appropriate gland and housing dimensions, thus providing the desired end performance. Iterative testing processes also can be used to fine tune gland performance. Computer simulation tools can further enhance the testing process. For example, the performance of the gland 28 can be modeled by finite element software ("FEA" software), such as ABAQUS EXPLICIT FEA software, distributed by Abaqus East LLC of Warwick, R.I.

In use, it is anticipated that the neutral design (i.e., the design where the gland 28 maintains substantially the same volume as it transitions between positions) may have some error factor that causes negligible amounts of fluid drawback or positive push through its outlet 16. Such negligible amounts, however, only should have negligible impact on the general goals of a neutral design.

Moreover, some embodiments may coat the interior of the housing 14 with a conventionally available anti-bacterial coating to further protect its sterility. Alternatively, conventional anti-bacterial material can be incorporated directly into the housing or gland materials.

Some embodiments of the invention have more than the three noted components (i.e., proximal housing portion 13, distal housing portion 15 with integrated post member 20, and gland 28). For example, the valve 10 also may include a gland securing member 80 within its interior to further secure the sealing ring 60 within its interior. Of course, illustrative embodiments integrate such member into the distal housing portion 15.

Accordingly, in illustrative embodiments, radial inward stress (also referred to in the art as "hoop stress") applied to the sealing ridge 58 normally occludes fluid flow through the valve 10. Moreover, the volume of the dynamic portion 64 of the fluid path substantially eliminates fluid drawback through the valve 10.

Figure 5:
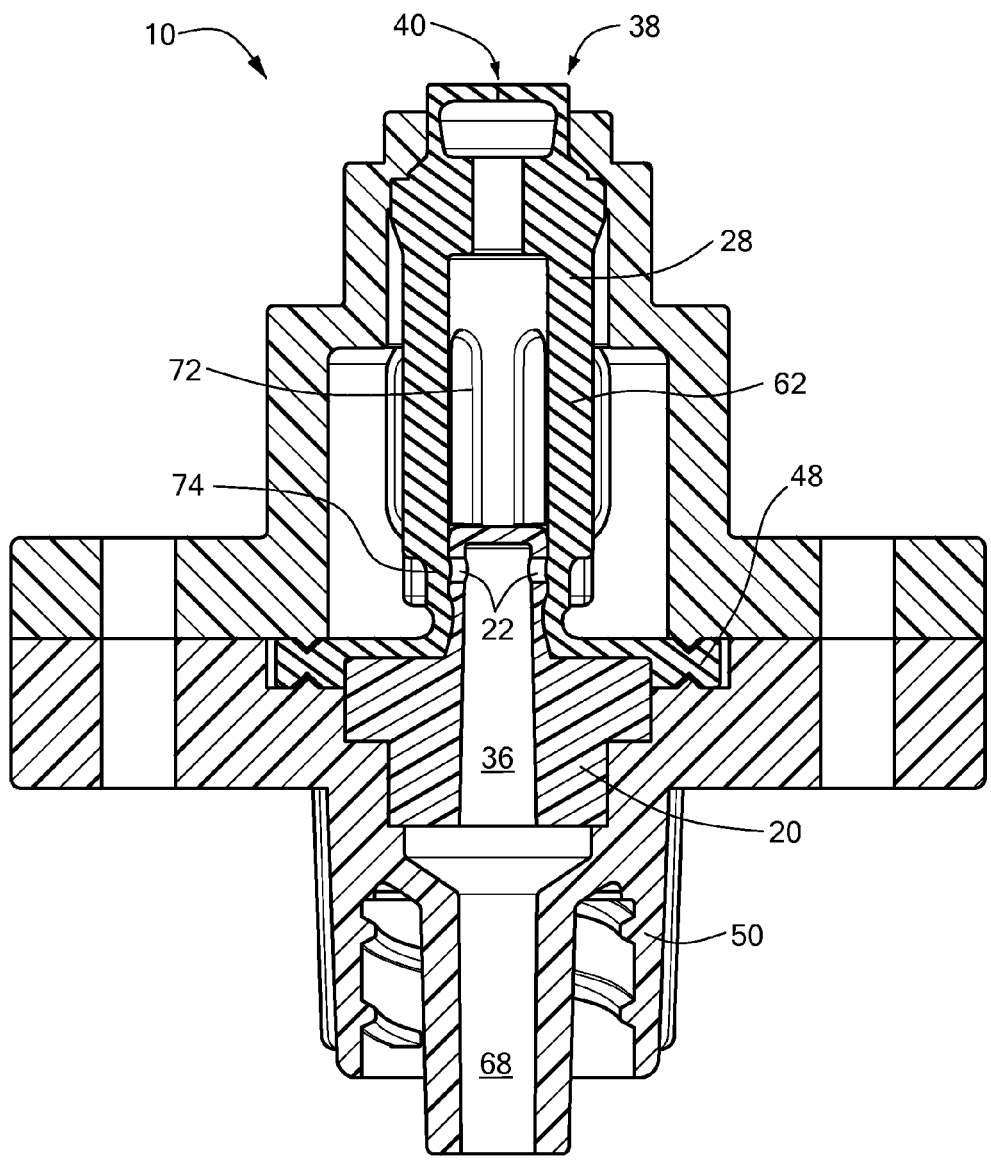
FIG. 5 schematically shows a cross-sectional view of the medical valve of FIG. 1 along line X-X in accordance with a fourth embodiment of the invention.

FIG. 5 schematically shows a cross-sectional view of a fourth embodiment of the medical valve 10 (along line X-X of FIG. 1) in a closed position. More particularly, FIG. 5 schematically shows a cross-sectional view of an embodiment of the medical valve 10 shown in FIG. 1, which also is configured to substantially eliminate fluid drawback during a withdrawal stroke. As noted above, this reduction can result in either a positive pressure at the distal port 16, or a zero net pressure at the distal port 16.

Among other things, the valve 10 includes a housing 14 containing a resilient, compressible, and stretchable gland 28. More specifically, the housing 18 includes a proximal housing portion 13 coupled with a distal housing portion 15 incorporating a post member 20. Any conventional coupling means may be used, such as ultrasonic welding or conventional snap-fit techniques. The gland 28 and post member 20 cooperate to control fluid flow through the valve 10. In illustrative embodiments, the gland 28 is secured within the valve 10 between the two housing portions. Details of the interaction of the post member 20 and the gland 28 are discussed below.

In the embodiment shown in FIG. 5, the post member 20 has a closed, convex proximal end and a transverse channel 34 that leads to an internal post member flow channel 36. In a manner similar to other embodiments, the post member flow channel 36 merges into a distal flow channel 68 that terminates at the distal port 16. Accordingly, the gland 28 normally is pre-loaded to occlude the transverse channel 34, thus preventing fluid flow. Application of a downward pressure (e.g., by a nozzle) causes the gland 28 to separate from the transverse channel 34, consequently opening the valve 10. When open, fluid can flow into the post member 20 via 1) the transverse channel 34, 2) through the post member flow channel 36, 3) through the distal flow channel 68, and 4) out the distal port 16.

In a manner similar to other embodiments, the gland 28 is the only movable part within the interior of the valve 10. To that end, the gland 28 has a swabbable seal section 38 having a normally closed slit 40 therethrough, a main section 62 extending from the seal section 38 to its base, and a radial attachment section 48 that secures the gland 28 within the valve 10. In accordance with illustrative embodiments of the invention, the main section 62 has a relatively thick main wall 70 with a plurality of radially protruding lobes 72. The lobes 72 preferably have thinner walls than those of the main section 62 (i.e., the main walls 70). Consequently, the lobes 72 should expand with less resistance than the main wall 70. Accordingly, the lobes 72 should radially expand a greater distance than that of the main section walls 70. Details of this portion of the gland 28 are discussed in greater detail below.

The main section 62 of the gland 28 also has an occluding portion 74 that normally occludes the transverse channel 34, consequently acting as the noted second seal when in the closed mode. The valve 10 thus has two seal areas; namely, the seal at the transverse channel 34 and the slit 40 in the seal section 38. Accordingly, when closed, which is its normal state, the valve mechanism uses its two redundant seals to prevent fluid communication between the proximal and distal ports 12 and 16. Specifically, when closed, the gland 28 prevents fluid flow through the transverse channel 34, while the slit 40 prevents fluid flow through the seal section 38.

In some embodiments, the gland/transverse channel seal can withstand higher backpressures than those that the slit 40 can withstand. To that end, the occluding portion 74 may be formed to have about a 0.010 inch interference fit against the post member 20. In addition to enabling the valve 10 to withstand higher backpressures, the fit of the occluding portion 74 against the post member 20 also should be selected to open the transverse channel 34 at an appropriate point in the opening stroke of the valve 10.

Figure 6:
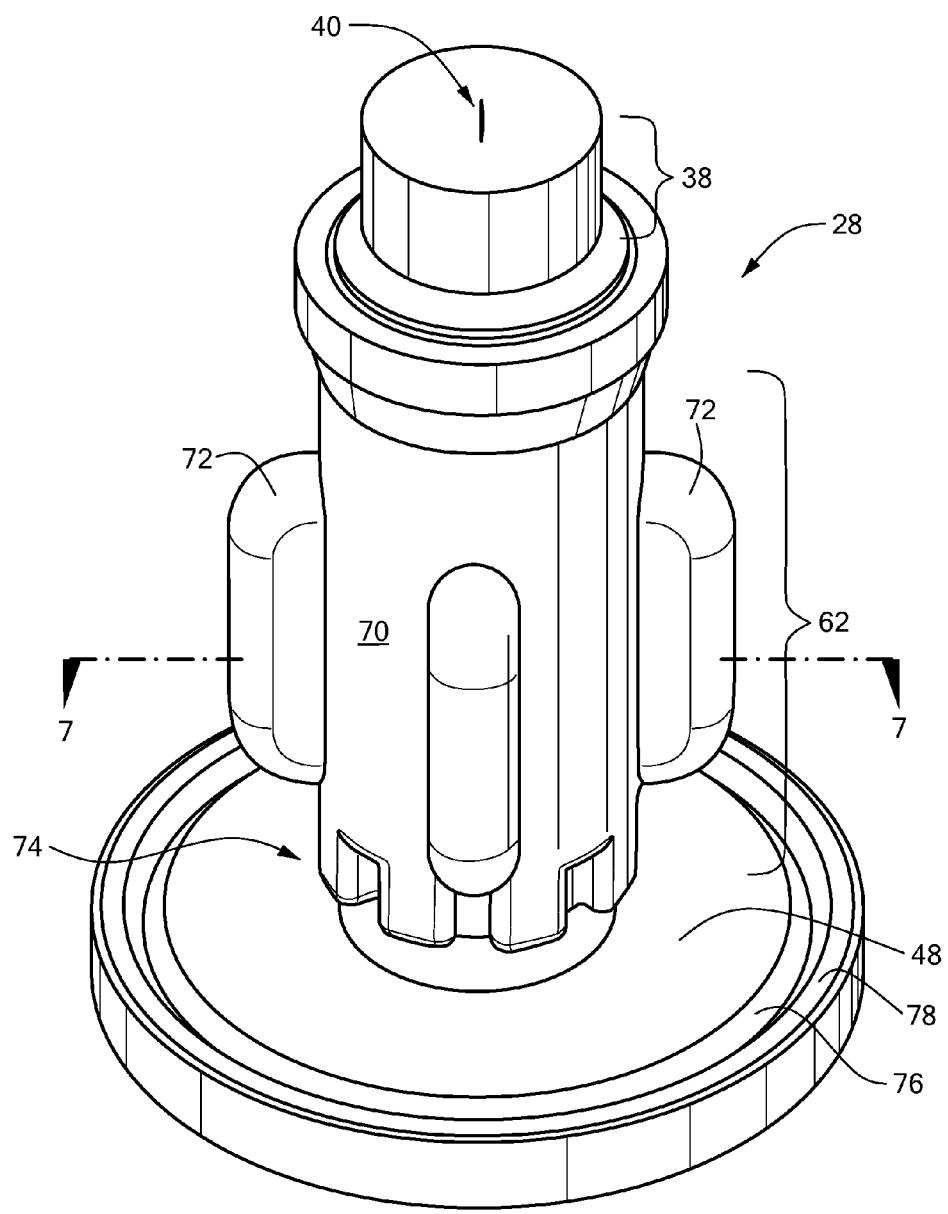
FIG. 6 schematically shows a perspective view of a gland member of the valve shown in FIG. 5.

FIG. 6 schematically shows a perspective view of the gland 28 shown in FIG. 2. As shown, the gland 28 has four lobes 72 extending from the main section 62. Each of the lobes 72 is radially spaced about ninety degrees from two other lobes 72 along the main section 62. In alternative embodiments, rather than being spaced around the circumference of the gland 28, the lobes 72 may be longitudinally spaced. In other words, the gland 28 may have two or more lobes 72 spaced along its longer dimension. Moreover, the attachment section 48 has a circumferential ridge 76 and flange 78 to further secure the gland 28 within the valve 10.

Figure 7:
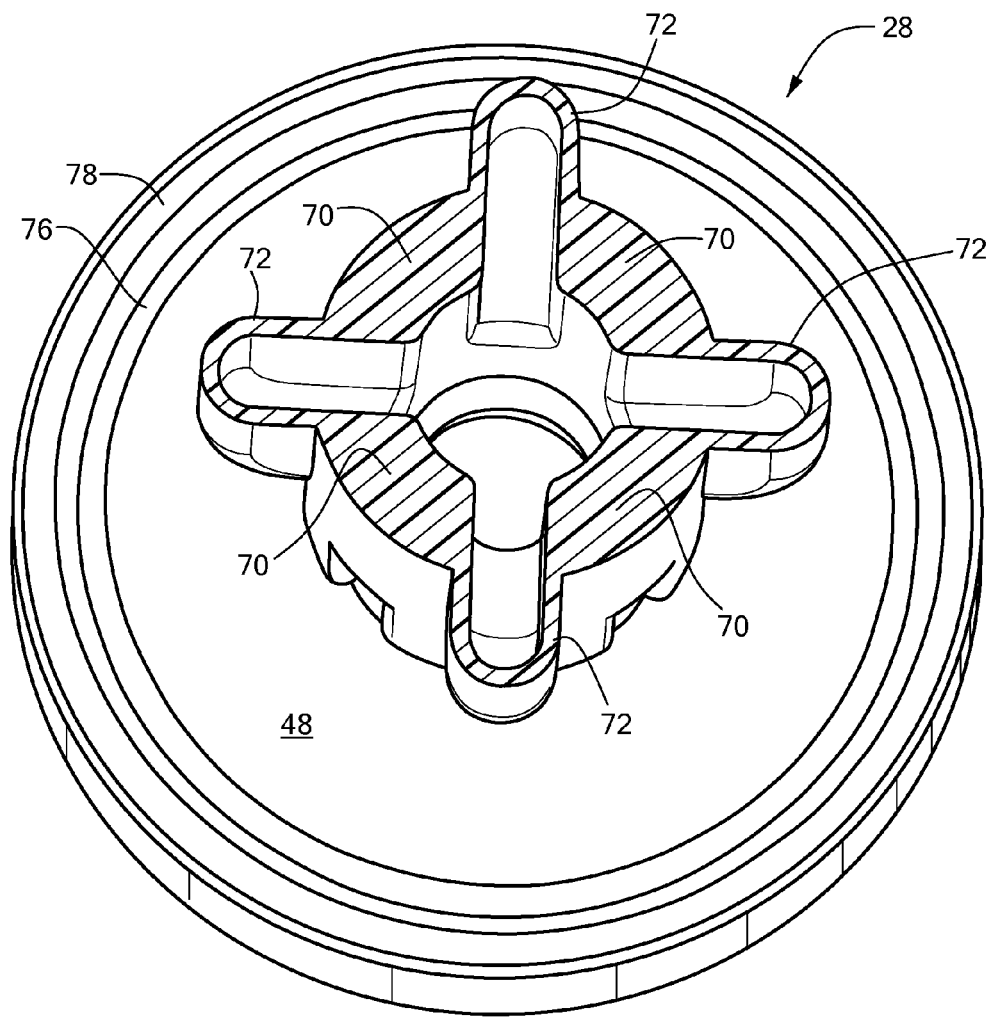
FIG. 7 schematically shows a radial cross-sectional view of the gland member shown in FIG. 6 along line 7-7.
Figure 8:
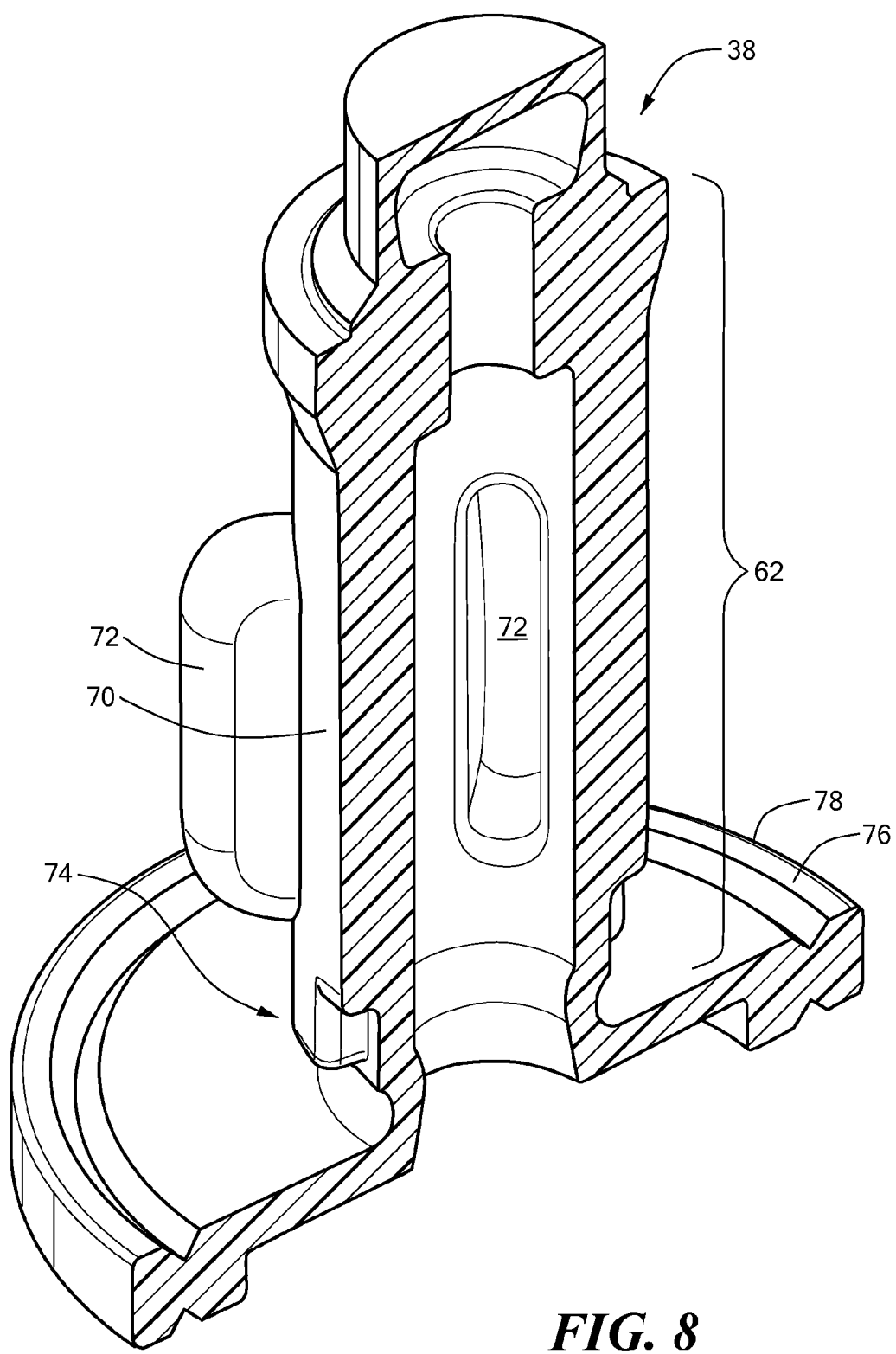
FIG. 8 schematically shows a longitudinal cross-sectional view of the gland member shown in FIG. 6.

FIG. 7 shows the relative wall thicknesses of the lobes 72 and the main wall 70, while FIG. 8 shows the lobes 72 from the gland interior. As shown, the main walls are several times thicker than the lobe walls 70. For example, the lobe wall may be about 0.010 inches thick, while the main walls 70 may be about 0.053 inches thick. These relative thicknesses should provide a sufficient column strength to the gland 28 to minimize its likelihood that it will collapse when compressed. Instead of collapsing entirely, the lobes 72 should expand radially to some extent, while the main wall 70 substantially maintains its radial position (subject to some expansion or deformation that does not adversely affect valve operation). In some embodiments, however, the main wall 70 also expands radially as the lobes 72 expand.

Insertion of a nozzle against the slit 40 at the proximal end of the gland 28 causes the seal section 38 to both compress and move distally. Consequently, the slit 40 opens and the seal section 38 both axially compresses and radially expands. In a similar manner, the main section 62 both axially compresses and radially expands. Specifically, the lobes 72 radially expand, while the main walls 70 radially expand much less significantly.

It is anticipated, however, that the lobes 72 attain a maximum volume before the nozzle is fully inserted into the valve 10. After that point, the lobes 72 axially compress to some extent, which may produce some positive pressure from the interior of the lobes 72. In a corresponding manner, when withdrawing the nozzle from full insertion, it is anticipated that the lobes 72 actually may expand to some extent before contracting. Accordingly, during nozzle withdrawal, some negative pressure may draw fluid into the valve 10. Despite these imperfections, it is anticipated that the lobes 72 ultimately will produce the desired anti-drawback effect by the time the nozzle is fully withdrawn from the valve 10. The negative impact of the noted lobe compression thus is expected to have a negligible effect on the overall operation of the valve 10.

At some point in the transition from the closed mode to the open mode, the occluding portion 74 of the gland 28 no longer contacts (i.e., no longer occludes) the transverse channel 34, consequently fully opening the valve 10. When open, the volume of the variable volume region is based upon the noted gland axial compression and radial expansion. In illustrative embodiments, the materials and dimensions of the gland 28 are selected to ensure that 1) both the open and closed volumes are substantially equal, or 2) the open volume is greater than the closed volume.

When the volumes are substantially equal, there should be no appreciable positive or negative net pressure at the distal port 16 when the nozzle is withdrawn. Accordingly, in such case, only negligible amounts of fluid drawback or distally directed pressure, if any, should occur. Conversely, when the open volume is greater than the closed volume, a net positive pressure develops at the distal port 16 when the nozzle is withdrawn. Accordingly, in that case, an appreciable amount of fluid within the valve 10 is expelled from the distal port 16. Expelling the fluid should prevent fluid from being drawn into the valve 10 at that time.

The valve 10 may be manufactured in accordance with conventional processes. In a manner similar to other embodiments, the housing 14 and post member 20 may be produced from a rigid plastic, while the gland 28 may be formed from a medical grade elastomeric material, such as silicone or rubber. Moreover, the post member 20 may be a separate piece inserted into the outlet portion of the housing 14, as shown in FIG. 5, or it may be integral with the housing 14. In the latter case, the post member 20 is considered to be a part of the housing 14. This also applies to other embodiments.

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow through an internal flow path, the medical valve also having a closed mode that prevents fluid flow through the internal flow path, the medical valve comprising:
   a housing forming an interior containing the flow path;
   a post member within the interior, the post member having a lumen that is a part of the flow path and a solid wall surrounding and defining the lumen, the lumen having an opening to the interior of the housing; and
   a gland member circumscribing the post member to form a variable volume region, the variable volume region being formed at least in part between the gland member and the post member, the variable volume region being a part of the flow path, the gland member having a protrusion extending into and occluding the post lumen opening when in the closed mode, at least a portion of the post member lumen extending into the gland member,
   the variable volume region having a closed volume when in the closed mode,
   the variable volume region having an open volume when in the open mode,
   the open volume being no less than the closed volume.

2. A medical valve according to claim 1, wherein the protrusion is a sealing ridge, the sealing ridge extending to the post lumen opening.

3. A medical valve according to claim 1, wherein the protrusion and the post lumen opening have complimentary shapes.

4. A medical valve according to claim 1, wherein the variable volume region is closed when in the closed mode.

5. A medical valve according to claim 1, wherein the housing has a proximal port, the gland member having a proximal end that is substantially flush with or extends proximally of the proximal port.

6. A medical valve according to claim 1, wherein the protrusion moves out of the post member lumen opening as the valve transitions from the closed mode toward the open mode, thereby unoccloding the post lumen opening.

7. A medical valve according to claim 1, wherein the open volume is greater than the closed volume.

8. A medical valve according to claim 1, wherein the open volume is substantially equal to the closed volume.

* * * * *